United States Patent [19]

George

[11] Patent Number: 4,933,886

[45] Date of Patent: Jun. 12, 1990

[54] DEVICE FOR MEASURING MELT FLOW INDEX

[76] Inventor: Alan George, 238 Alwyn Road, Bilton, Rugby, Warwickshire, England, CV22 7RR

[21] Appl. No.: 252,133

[22] Filed: Oct. 3, 1988

[30] Foreign Application Priority Data

Oct. 1, 1987 [GB] United Kingdom ............... 8723101

[51] Int. Cl.⁵ .................. G06F 15/46; B29H 5/02
[52] U.S. Cl. .................. 364/556; 364/473; 364/476; 364/510; 364/477; 374/54; 264/40.6; 73/53
[58] Field of Search .............. 364/473, 476, 477, 500, 364/510, 556, 557; 374/53, 54; 264/40.1, 40.6; 73/53, 54, 56

[56] References Cited

U.S. PATENT DOCUMENTS

| | | | |
|---|---|---|---|
| 2,934,944 | 5/1960 | Eolkin | 73/55 |
| 3,048,030 | 8/1962 | De Haven | 73/56 |
| 3,138,950 | 6/1964 | Welty et al. | 73/55 |
| 3,209,581 | 10/1965 | Crane et al. | 73/55 |
| 4,241,602 | 12/1980 | Han et al. | 73/56 |
| 4,344,142 | 8/1982 | Diehr, II et al. | 364/473 |
| 4,515,545 | 5/1985 | Hinrichs et al. | 364/476 |
| 4,534,003 | 8/1985 | Manzione | 364/476 |
| 4,546,438 | 10/1985 | Prewitt et al. | 364/473 |
| 4,551,807 | 11/1985 | Hsich et al. | 364/476 |

FOREIGN PATENT DOCUMENTS

| | | |
|---|---|---|
| 0013594 | 7/1980 | European Pat. Off. |
| 0210689 | 2/1987 | European Pat. Off. |
| 755613 | 8/1956 | United Kingdom |
| 985447 | 3/1965 | United Kingdom |
| 1552082 | 9/1979 | United Kingdom |

OTHER PUBLICATIONS

"Application of Microprocessors in Devices for Instrumentation and Control", *A Process Analyser with a Versatile Microcomputer Control and Readout System*, 1980, IMEKO Conference, pp. 211–231.

Primary Examiner—Parshotam S. Lall
Assistant Examiner—Brian M. Mattson
Attorney, Agent, or Firm—Young & Thompson

[57] ABSTRACT

A melt flow index measurement device includes a sample enclosure (125), a loading device (90) for applying a sample under pressure to the enclosure, a pressure sensor (112) for determining the pressure within the enclosure upstream of the restriction, an output port (130) in the enclosure downstream of the restriction, and a temperature control (91, 92, 76) and monitoring system for determining the sample temperature within the enclosure. A data processor computes the melt flow index from successive measurements of pressure and flow rate through the output orifice or restriction under operating conditions, and derives from those computations the melt flow index of a sample under a predetermined set of standard conditions.

3 Claims, 6 Drawing Sheets

DEVICE FOR MEASURING MELT FLOW INDEX

This invention relates to rheometric measurement, that is measurement of the rheological properties or characteristics of a material, i.e. its flow and deformation, and is particularly, but not exclusively concerned with the measurement of so-called melt flow index, this being one of the key factors in determining the behavior of material when being 'worked' into a manufactured form by applied stress.

Another such key characteristic is viscoelasticity, the measurement of which is the subject of our pending UK patent application No. 8723796

Together, melt flow index and viscoelasticity may be said to define comprehensively the rheological properties of a material and are in practice all that is needed to identify performance characteristics and predict the behavior of a material when it is 'worked' in manufacture, for example, extruded or molded in the case of a synthetic plastics material from a melted and flowing ingredient.

In that regard, although the present invention is particularly concerned with melt flow index, the combined simultaneous measurement with viscoelasticity is possible by incorporating a supplementary measurement chamber in the same general controlled-environment mounting block, as discussed in our pending UK patent application No. 8723796.

There is prescribed by the relevant standards authorities a standard or reference set of test conditions for measurement of melt flow index (or MFI, by which abbreviation it will hereinafter be referred and identified).

MFI is a factor of interest both to producers of bulk 'raw' plastics ingredient, for example granules, chips or powders, for subsequent manufacture, and the end-users themselves, who have to set their machines to suit the material input ingredient and the desired end-product. The structural and aesthetic characteristics can be impaired if the incorrect conditions are used.

Thus, the early recognition of material characteristic departures from the desired standard, and the prompt initiation of corrective control action—for example, revised machine settings—offers significant enhancements in the economics and quality of manufacture.

This is particularly so if the cycle of (input) monitoring and (output) control is 'closed', i.e. there is automatic feedback of corrective control action.

Analog techniques for achieving this typically require elaborate circuitry with skilled and delicate setting up and adjustment in running. An MFI measurement technique that will be compatible with more 'robust' digital control is thus desirable.

However, the measurement of MFI has hitherto proved difficult under routine manufacturing, as opposed to carefully and strictly monitored, environmental—controlled laboratory conditions. This is particularly so for MFI's over a wide range when consistent evaluation is required.

There have been various earlier proposals for MFI measurement, using diverse forms of device. For example, U.S. Pat. No. 3,048,030 teaches the continuous measurement of MFI at constant flow rates by monitoring pressures upstream of the flow. Similarly, U.S. Pat. No. 3,209,581 is concerned with a continuous melt indexer.

On the subject of rheometrics generally, early liquid measurement proposals, such as U.S. Pat. No. 2,023,309, have addressed the problem of viscosity measurement in lubrication systems.

According to one aspect of the invention there is provided a viscosity or melt flow index measurement device comprising: a sample enclosure, loading means for applying a sample under pressure to the enclosure, a restriction within the enclosure, monitoring means for determining the pressure within the enclosure upstream of the restriction, an output port in the enclosure downstream of the restriction, temperature control and monitoring means for determining the sample temperature within the enclosure, control means for initiating and repeating a test cycle under various pressure and flow conditions for a given temperature, measuring means for measuring the pressure and flow conditions within the enclosure, data processing means for computing the viscosity or melt flow index from successive measurements of pressure and flow rate through the output orifice or restriction.

According to another aspect of the invention, there is provided a viscosity or melt flow index measurement device, as set forth in the immediately preceding paragraph, incorporating simulation means for simulating the standard derivation of viscosity from measurement of flow rate at a fixed pressure, by effecting a plurality of pressure drop measurements across an orifice through which various rates of flow are deliver, in particular by applying pressure, through a ram extrusion process, and controlled temperature conditions to provide a polymer melt flow, generating and expressing, in digital terms, an algorithm representing the predicted theoretical relationship between pressure and flow and manipulating derived measurement data in logarithmic form to compute, generate and plot graphically the relationship between flow rate and pressure and therefrom to form a notional intercept with a computer-generated reference line of constant pressure related to the standard viscosity measurement test condition profile and deriving the viscosity from that intercept by a technique of successive approximations involving comparisons between the local values of the constant reference pressure line and the plot of measured pressure and flow rate for a range of flow rate and repeating the comparison until equality is achieved.

According to a further aspect of the invention, the apparatus as set out in either of the two immediately preceding paragraphs incorporates an interchangeable restriction nozzle head, whereby MFI measurement over a substantial range can be accommodated simply by selecting a head of the appropriate scale; the in-built circuitry performing the necessary calculation adjustment when the head selection is input as a control setting.

In this way the usual constraints of extremely low flow rates over a long measurement time interval or extremely high flow rates. There is, moreover, not the difficulty of arriving at correct temperature conditioning. Rather, the range of interchangeable orifices, (flow) restrictions or nozzles admit of readily achievable flow rates and pressures equivalent to the prescribed standard MFI measurement pressure.

The invention also facilitates the measurement of MFI over a wide range by the use of a succession of differently—sized orifices, each with overlapping range measurement suitability to the next adjacent orifice size in the range, and with provision for numerical scaling adjustment of the computation settings.

The terms nozzle, restriction, jet and orifice are used herein somewhat interchangeably.

The measurement may be effected directly from the output of a ram or screw (auger) extruder for granular or powder ingredients without further melting if the output stream is already molten.

Indeed, a very compact construction is possible with a vertical measurement flow path (i.e. the orifice discharging under gravity) aligned below a vertical, horizontal or inclined ram or a horizontal extruder; with an integrated measurement flow control pump (e.g. gear pump) and controllable drive motor (e.g. stepper motor).

The provision of a short measurement flow path ensures a short time lag for the transition of a sample through the measurement process and a rapid turn-around from one sample to the next.

There now follows a description of some particular embodiments of the invention, by way of example only, with reference to the accompanying essentially diagrammatic and schematic drawings, in which:

Thus FIG. 2 is effectively a section taken along the line 2-2' in FIG. 3 and FIG. 1 along the line 1-1'.

Referring to the drawings, a melting chamber assembly, indicated generally by reference 35, is located in a recess in the upper surface of a homogeneously temperature-controlled mounting block 70, which is surrounded by a heater collar or cuff 71.

Figure 3:
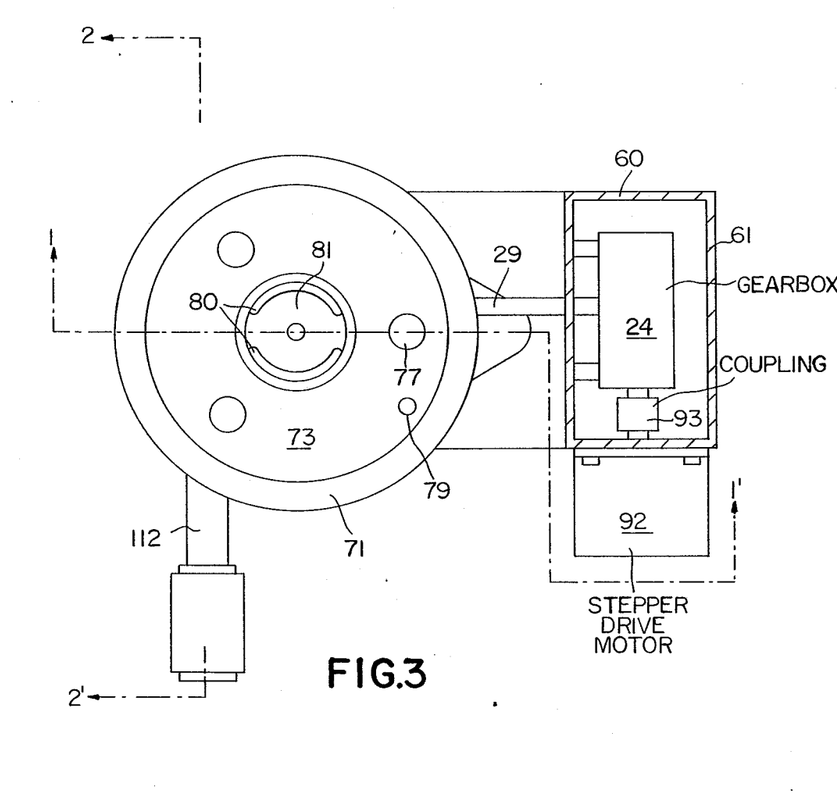
FIG. 3 shows a plane view of the apparatus shown in FIGS. 1 and 2, taken at selectively different levels.

A gear pump 25 is located in a side recess in the block 70 and is driven through a shaft 29, a (reduction) gearbox 24, a coupling 93 and a stepper drive motor 92, which are more clearly illustrated in FIG. 3.

Figure 2:
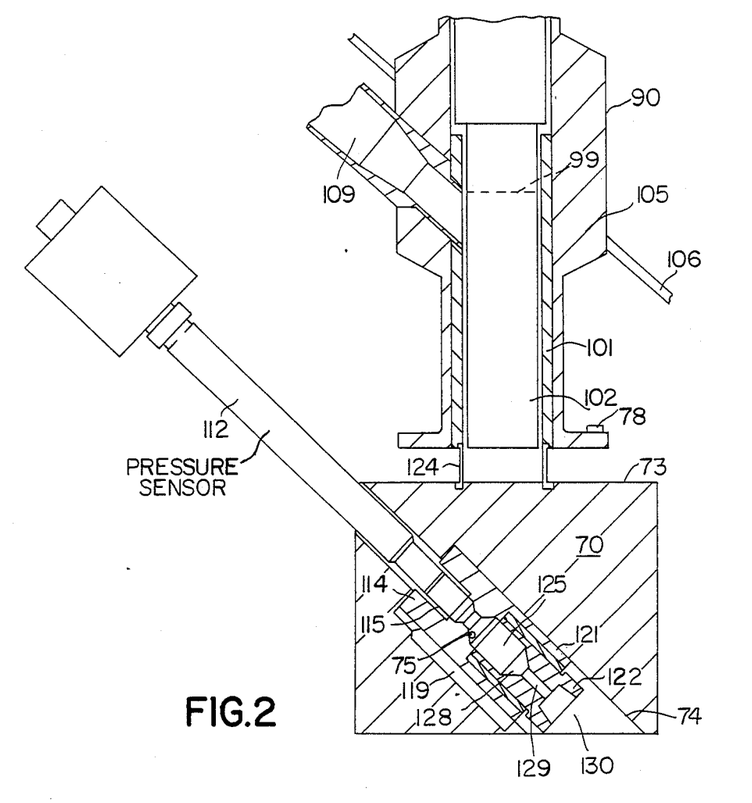
FIG. 2 shows a sectional end elevation of the apparatus shown in FIG. 1.

The block 70 is generally cylindrical and is surmounted by an upright ram extrusion 90 assembly, for ease of illustration only, depicted in FIG. 2.

The ram assembly 90 comprises a thermally-insulated (hard-sleeved) cylinder 101, with an outer insulating jacket collar or sleeve 105, and an internal axially-slidable piston 102, the upper limit of whose travel—representing an intake position—is indicated by broken line 99. The latter is just above an intake passage 109 through which 'raw' material sample is fed, for example from a supply hopper (unshown).

The cylinder, with an upper panel mounting 106, is located upon the upper mounting surface 73 of the block 70 and secured in position by bolts 78 received in threaded bores 77 in the upper surface 73 thereof. An insulating collar 124 separates the cylinder 101 from thermally-conducting contact with the block 70, so that the assembly 90 will not act as a local heat sink and disturb the temperature homogeneity of the block 70.

The ram assembly 90 supplies a 'shot' of material to a test chamber 125 defined within a removable die insert 122, which incorporates a precisely defined orifice or flow passage restriction 129, scaled according to the MFI range under measurement.

The orifice 129 communicates with the test chamber 125 through a carefully graduated tapered bore 128, which does not disturb the laminar material flow into the orifice 129.

After test the material simply discharges through a waste aperture 120 into a collection bin (unshown).

The insert 122 is located within a carrier sleeve 121, which is in turn a snug fit in an obliquely-angled bore 74 in the underside of the block 70 and is secured in position through a locking pin 119. The upper end 114 of the sleeve 121 has a bore 115 in which is received the end of a pressure-sensing transducer probe 112. In this way, different orifices 129 can readily be used by inserting the relevant insert 122.

Although an inclined (to the vertical) discharge path is illustrated for the orifice 129, a vertical path may be arranged, so that the discharge is more effectively under the influence of gravity, thereby better to meet the prescribed test conditions (in particular, no undue restrictions on final outflow from the orifice).

Figure 1:
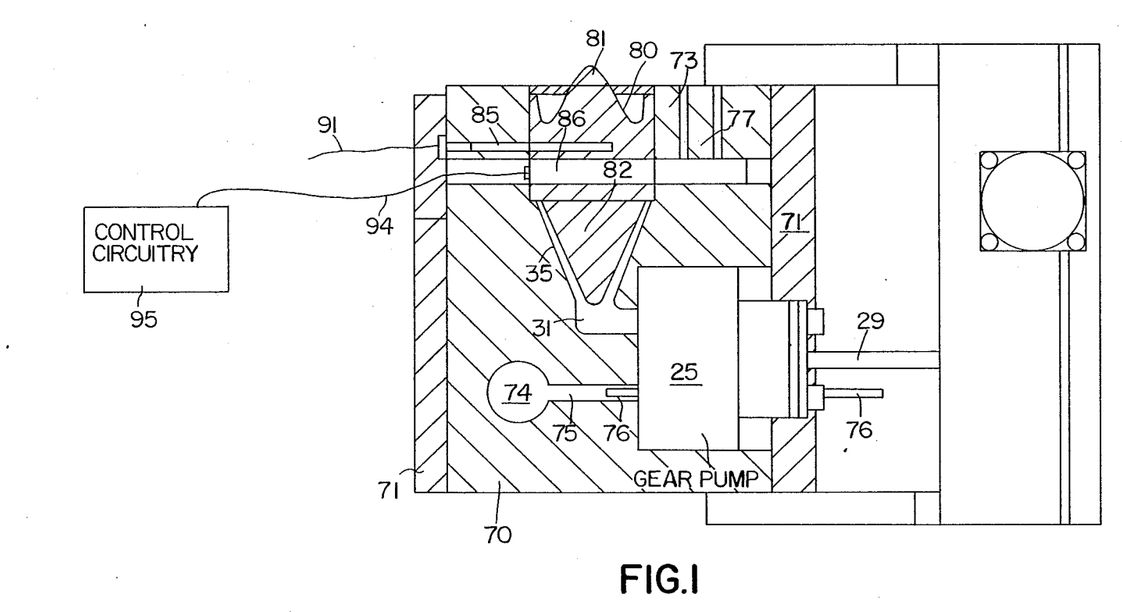
FIG. 1 shows a sectional elevation of the MFI section of a rheometric apparatus.

As can more clearly be identified in FIG. 1, a fill hole 75 accesses the head of the chamber 125 and receives material delivered from the gear pump 25 and which has in turn been driven from the intake ram assembly 90 through a temperature monitoring and control station 35. The latter incorporates a melter 82 of high thermal conductivity material and whose head 81 is specially contoured to deflect raw material ingredient input under high pressure from the ram piston 102. Opposed segmented annular slots 80 allow passage of material from the head down to the tapered foot and funnel-shaped outflow of the melter 82.

A heater element 86 is fitted into a transverse bore in the melter and has an electrical supply lead 94 connected to control circuitry 95. Similarly, a resistance thermometer 85, with a monitoring lead 91, is mounted in the melter 82 just above the heater 86.

The combination of high ingestion pressure and heat at the melter head 81 is sufficient to ensure melting of the material and the exclusion of air pockets. Thus, granular or powder raw material intakes can be accommodated.

Temperature is maintained by mounting the gear pump 25 itself largely within the block 70 and thus within the confines of the heater cuff 71. Thus, the gear pump 25 is the means of metering precise flow rates at prescribed 'melt' test temperatures. An auxiliary thermometer 79 is buried in the head 73 of the block 70 and linked to the temperature monitoring and control circuitry 95 of FIG. 1 in order to facilitate the feedback control cycle.

In addition, a melt thermometer 76 is inserted through the gear pump 25.

The stepper motor 92 is set to run at either of two predetermined controlled speeds.

The structural disposition of components is such that there is a low time lag in the passage of material delivered at precise temperature and flow conditions to the test chamber 125 for transition through the orifice 129.

Figure 4:
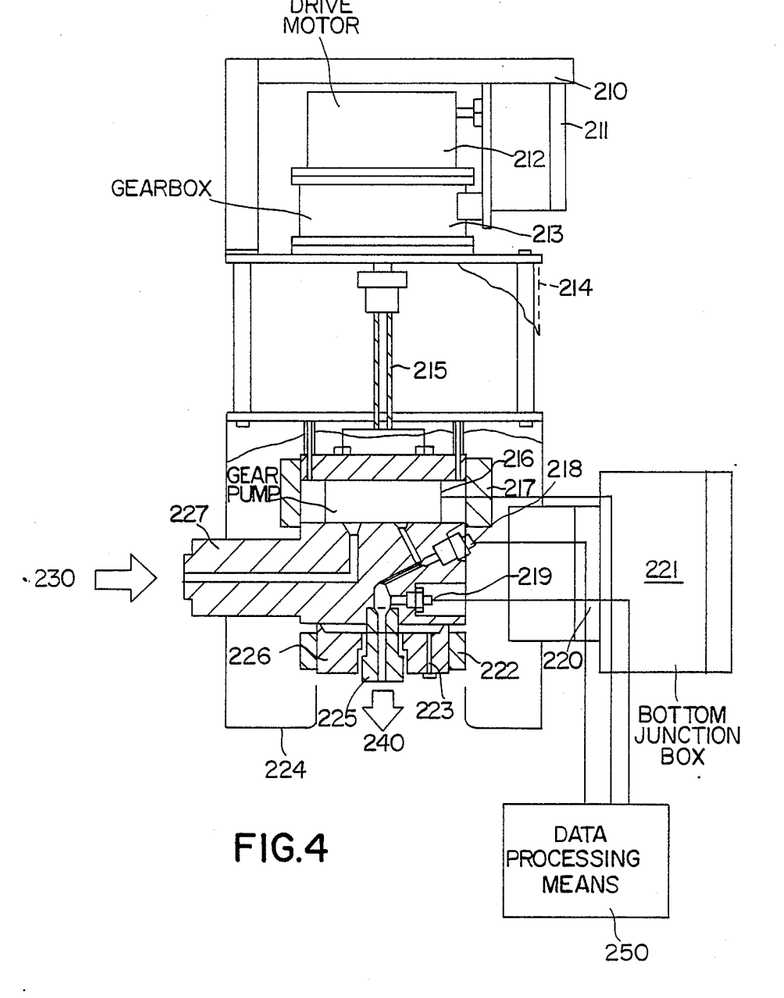
FIG. 4 shows an alternative MFI measurement apparatus (without integral melter) layout to that shown in FIGS. 1 to 3.

If the measurement apparatus is fitted directly to the output of an extruder, the measurement pre-melter stage may be omitted, as shown in FIG. 4.

Referring to FIG. 4, an inflow of material 230 from a horizontal extruder is fed to a pump 216 connected by a drive shaft 215 to a gearbox 213 and a drive motor 212.

The output of the pump 216 is fed to a top zone thermometer 218 and then to a pressure transducer 219 upstream of a jet 225 mounted in a bottom block 226 with its own bottom zone heater shroud 222 and bottom zone thermometer 223; output 240 being discharged vertically after test.

A heat shield 210 enshrouds the motor 212 and gearbox 213, and a protective guard 214 covers the drive shaft 215. A top junction box 211 makes the electrical connection with the motor 212 and a bottom junction box 221 with the various heaters, transducers and thermometers.

A metal foam block 220 isolates the bottom junction box 221 from a main cover 224 for the measurement block.

Although not presently described in detail, the circuitry for the measurement apparatus, such as that shown schematically at 250 in FIG. 4, would incorporate a computer, with a display of pressure, MFI and flow number (FN), related to MFI by the formula previously quoted. Departure from the required value may also be indicated. Feed of the measurement sample would be through pulses applied to the (stepper) drive motor to increment the (gear) pump of known capacity a prescribed amount in a given interval. A successive approximation technique may be used to determine the pressure and/or flow rates by applying a progressively incremented or decremented pulse amplitude to a monitored digitized transducer value and monitoring the change from positive to negative arithmetic subtraction or comparison of the generated and derived pulse streams.

The prescribed standard MFI test is the measurement of the amount of material flowing through an orifice some 0.0825 inch (or 2.09 mm) diameter and having an L/D (i.e. length to diameter) ratio of 1/3.818, due to or arising from the force exerted by a displacement weight of 2.16 kg upon a ⅜ inch diameter (loading) rod at a regulated test temperature of 190 degrees C. or 230 degrees C. over a 10 minute period.

Each of the interchangeable orifices 129, in fact in a range of six, meets this standard L/D of 1/3.818 and the change in MFI produced by changing these orifices or jets 129 is derived from a formula relating the 'new' MFI to the product of the standard MFI and the cube of the ratio of the prevailing or current orifice diameter to the standard orifice diameter.

Viz: New MFI = Std. MFI * (new Diam./std. Diam.)

The MFI test computation relies upon a series of measurements for each orifice appropriate to the MFI range under test.

Specifically, the logarithm of the pressure monitored by the transducer 112 upstream of the orifice 129 is 'plotted' (or a computer-generated plot is derived) against the logarithm of the flow rate achieved by controlled driving of the gear pump 25 of known 'capacity' per cycle or revolution at a known rate.

Figure 5:
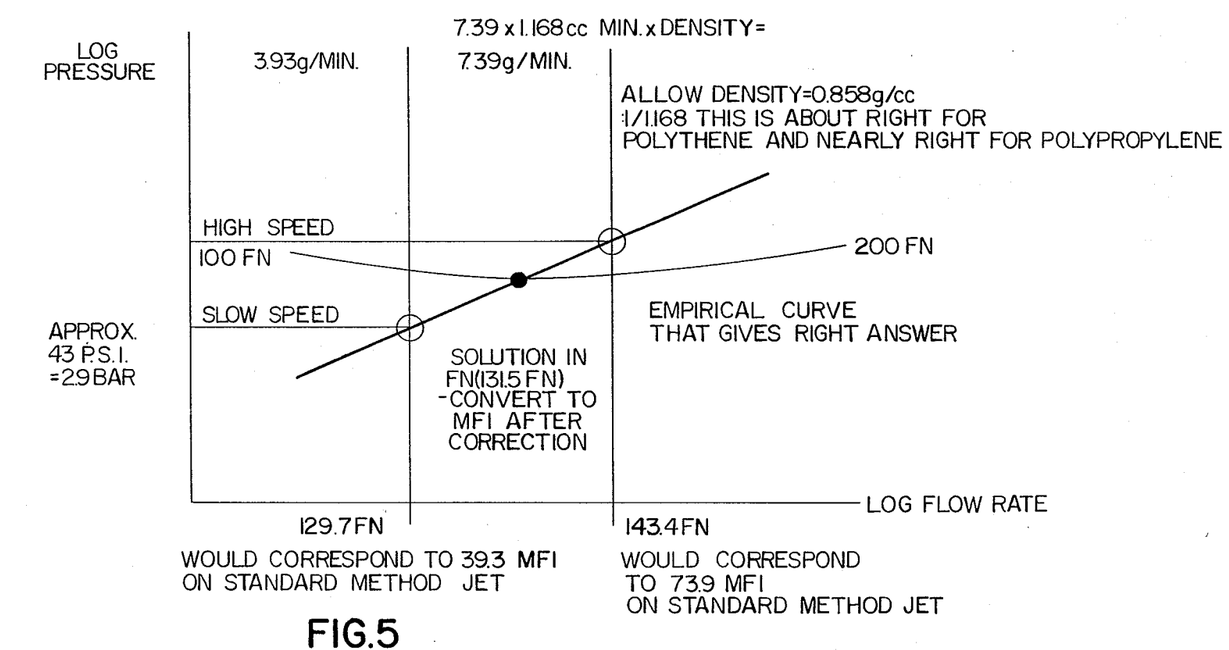
FIG. 5 shows graphically the performance of the apparatus shown in FIGS. 1 to 4.

Referring to FIG. 5, the resulting plot is essentially an empirical curve or 'nomogram' (i.e. providing the required answer— over a range of 100 FN to 200 FN) which approximates to a straight line (but allows for pressure drops generated at the entrance of the orifice from a 'settling' chamber) and from which the intercept of a constant reference pressure (approximately 43 p.s.i. or 2.9 bar) line, and at which intercept the flow rate is 'read off'. The intercept is determined by a technique of successive approximations involving comparisons between the local values of the constant reference pressure line and the plot of measured pressure and flow rate for a range of flow rates and repeating the comparison until equality is achieved.

The invention does not depend upon the following theoretical analysis, which is offered rather by way of background information, rather than the sole basis for the invention:

The steps in constructing a 'nomogram' are as follows:

(i) A curve is drawn on to log P (pressure) versus log flow rate graph, which 'fits' the relationship empirically;

(ii) Two readings of pressure are taken at two fixed 'speeds' (or flow rates—in fact 3.93 and 7.39 gm/min;

(iii) A straight line is drawn between these two points and intersects the 'curve' at 'x' flow numbers;

(iv) thus the 'solution is at 131.5 FN;

(v) a correction is made for 'jet' diameter; thus for a jet 9.7 mm diameter:

MFI correction = $(2.09/9.7)^3 = 1/100 = 2$ decades less than nomogram MFI;

therefore subtract 100 FN = 2 decades of MFI
($2 \times 50$)

(vi) corrected MFI = 31.5 FN

Note that the jet selected is to give reasonable pressure values at high and low speeds, within a factor of 2 of 43 psi.—ie. 86 psi or 21.5 psi.

These corrections are stored in the computer and called by the operator when a jet is selected.

The selection of jets is usually on a 10:1 MFI basis, with an overlap to allow continuity in operation in the margins.

```
0.2 MFI-*----------2 MFI------------5---------*-----50 MFI

.  1----------------*-------------10  .
         .  > 2:1 <    .   > 2:1 <  .
         .  overlap    .   overlap  .
         .             .            .
         jet dia.      jet dia.     jet dia.
         6 mm          4.8 mm       3 mm
```

Typical overlap for 3 jets to span 0.2 to 50 MFI.

NB. The delay of response is constant because the material flows at fixed rates for fixed times.

1.

If a constant pressure system is used, then more frequent jet changes are necessary if response time is to be made reasonable, ie. 3:1 range is normal; with overlap this requires 3–4 times number of jets.

```
0.2 MFI= = = =0.6 MFI
   0.3 MFI= = = = = =1.0 MFI
      0.5 MFI= = = = = = = =1.5 MFI
         0.75 MFI= = = = = = = = = =2.0 MFI . . . etc.
```

Flow number FN = $50(1 + \log_{10} MFI)$

2.

If a constant pressure system is used then the absolute accuracy of the system is degraded by:
(i) temperature equilibration, which is a function of pumping speed;
(ii) Actual pressure in system required to emulate test method varies as function of speed;

There is a need to program pressure as speed varies adaptively; either this is not done in simple systems—hence inaccuracies, or it has to be done in computer—with attendant additional complications.

It is possible to make measurements over a wide range of melt flow indices without the extremely low flow rates/long time of measurement or extremely high flow rates/difficulty of arriving at correct temperature conditioning by using a number of interchangeable orifices or jets that allow easily achievable flow rates and pressures equivalent to standard MFI pressure.

These orifices are scaled from the original 2.09 mm orifice which has a length/radius ratio of 7.636:1. This allows a shift in MFI according to the cube of the ratios of diameter. Moreover, the shape of the curve of the constant pressure line is constant—allowing interchange of orifices with a simple multiplier according to jet orifice size in relation to the 2.09 mm orifice.

Thus MFI intercept for a 4.18 mm orifice would have 8×equivalent flow rate of 2.09 mm orifice.

If the sequence of shear rates/flow rates is done over a fixed time scale, i.e. 2 mins at 4 g/min and 4 mins at 8 g/min, then the net flow rate is a constant. This gives a near constant response time for a measurement that covers 1 complete sequence.

A feature not available with constant pressure working:

If the MFI were to be measured with different orifice diameters using the constant pressure technique to 'cutoff' different weights after the 10 minutes of extrusion as specified in standard test, the range for an automatic measurement would be smaller than the range for the constant shear rates technique, typically 5:1 as opposed to 30:1 for the same degree of accuracy using the scaling between the two jets and taking into account the effect of errors of the measurement.

The main error of the MFI by constant pressure is the pressure transducer offset, but in the multiple shear method, the absolute zero is of less consequence because of the differential measurement effect of the measurement.

Figure 6:
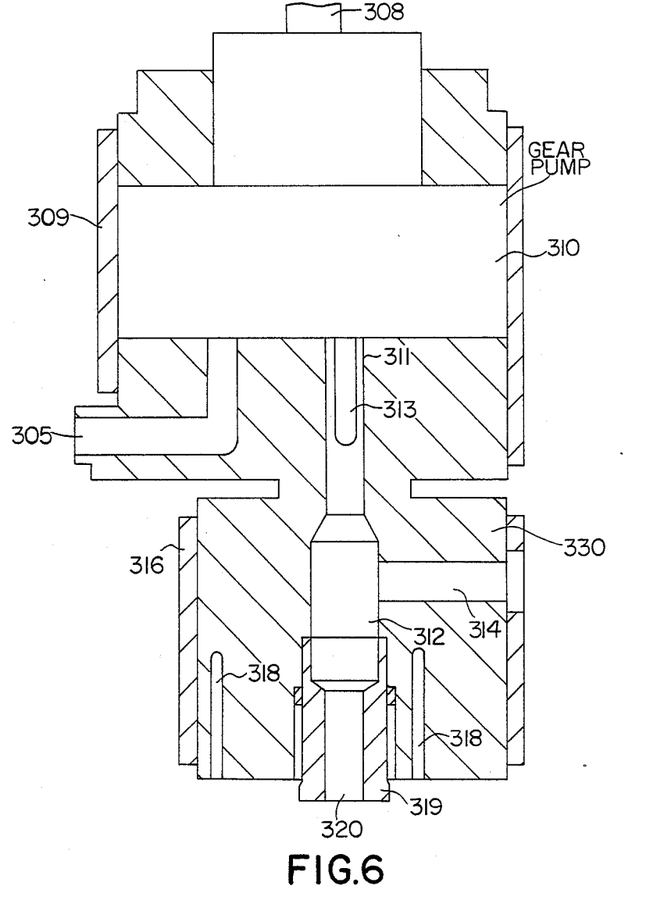
FIG. 6 shows an alternative compact arrangement to that of FIG. 1.

Referring to FIG. 6, a compact arrangement of an integrated gear pump and measurement chamber, suitable for fitting to, for example, a plastics extruder, is depicted.

The configuration is essentially circular in cross-section and thus, for a given (pump) capacity, occupies less space—which is advantageous in restricted installation situations.

The smaller overall mass of the development enables a desired operating temperature to be reached—and stabilized—more readily, with a homogeneous heat distribution. Thus, the operating condition of the measurement chamber is more strictly defined to prescribed limits.

The various features correspond to those already discussed in relation to FIGS. 1 to 5, and the primary features include:
a gear pump 310, closely coupled to a measurement block 330;
a gear pump drive shaft 308;
a pump inlet 305 for connection to a polymer source (eg. and extruder output or tapping);
a pump outlet 311—with an associated thermometer 313;
a pressure chamber 312—with an associated pressure sensor 314;
a polymer outlet 320 from the pressure chamber 312;
an orifice die block 319 defining the precise configuration and dimensions of the polymer outlet 320;
thermometer sets 318, set in the measurement block 330;
a cuff heater 316 around the measurement block 330; and a similar band heater 309 around the gear pump 310 itself.

I claim:

1. A melt flow index measurement device comprising:
means defining a sample flow path,
a sample enclosure (125) disposed in said sample flow path,
loading means (90) disposed upstream of said enclosure in said sample flow path for applying a sample under pressure to the enclosure,
an orifice (129) within the enclosure,
an output port (130) in the enclosure downstream of the orifice,
temperature control (91, 92, 76) and monitoring means in thermal communication with a portion of said sample flow path for determining a sample temperature within the enclosure,
measuring means so disposed on said device as to measure pressure and flow conditions within the enclosure,
data processing means in electrical communication with said measuring means, for evaluating a pressure and flow rate relationship from data acquired from repeated pressure and flow rate measurements performed by said measuring means over a range of varying flow conditions and deriving from the relationship the melt flow index of a sample under a predetermined set of flow conditions.

2. The melt flow index measurement device, as claimed in claim 1, further comprising simulation means for simulating a standard derivation of melt flow index from measurement of flow rate at a fixed pressure, by effecting a plurality of pressure drop measurements across an orifice through which various rates of flow are delivered, in particular by applying pressure, through an extrusion process, and controlled temperature conditions to provide a polymer melt flow, generating and expressing, in digital terms, a predicted theoretical relationship between pressure and flow and manipulating derived measurement data in logarithmic form to compute, generate and plot graphically a relationship between flow rate and pressure and therefrom to form a notional intercept with a computer-generated reference line of constant pressure related to a standard melt flow measurement test condition profile and deriving the melt flow from that intercept, by a technique of successive approximations involving comparisons between local values of the constant reference pressure line and the graphically plotted relationship of measured pressure and flow rate of a range of flow rates and repeating the comparison until equality is achieved.

3. The melt flow index measurement device, as claimed in claim 2, further comprising multiple interchangeable orifices for extended measurement range.

* * * * *